(12) United States Patent
Kjaer

(10) Patent No.: US 11,079,319 B2
(45) Date of Patent: *Aug. 3, 2021

(54) POROUS MIRROR FOR OPTICAL DETECTION OF AN ANALYTE IN A FLUID

(71) Applicant: RADIOMETER MEDICAL APS, Brønshøj (DK)

(72) Inventor: Thomas Kjaer, Smoerum (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/854,136

(22) Filed: Apr. 21, 2020

(65) Prior Publication Data

US 2020/0249151 A1  Aug. 6, 2020

Related U.S. Application Data

(63) Continuation of application No. 15/776,469, filed as application No. PCT/EP2016/077943 on Nov. 17, 2016, now Pat. No. 10,663,395.

(30) Foreign Application Priority Data

Nov. 18, 2015 (DK) .......................... PA 2015 00740

(51) Int. Cl.
*G01N 21/31* (2006.01)
*G01N 33/49* (2006.01)
(Continued)

(52) U.S. Cl.
CPC ........ *G01N 21/31* (2013.01); *B01L 3/502715* (2013.01); *G01N 33/49* (2013.01);
(Continued)

(58) Field of Classification Search
None
See application file for complete search history.

(56) References Cited

U.S. PATENT DOCUMENTS 5,580,744 A    12/1996  Zweig
6,040,191 A *   3/2000  Grow ..................... G01N 21/65
                                                      436/172
(Continued)

FOREIGN PATENT DOCUMENTS

CN       1255196 A      5/2000
CN     102046074 A      5/2011
(Continued)

OTHER PUBLICATIONS

Archibong, Edikan et al., "Optofluidic spectroscopy integrated on optical fiber platform," Sensing and Bio-Sensing Research, vol. 3, pp. 1-6 (2015).
(Continued)

*Primary Examiner* — Shawn Decenzo
(74) *Attorney, Agent, or Firm* — Finnegan, Henderson, Farabow, Garrett & Dunner, LLP

(57) ABSTRACT

A porous mirror (1) for detection of an analyte (96) in a fluid (99) by optical probing, comprising a translucent slab (2) with a front side (3), and a backside (4) facing away from the front side (3), wherein the front side (3) is adapted for being contacted with a fluid (99), and a reflective layer (5) at the front side (3) of the translucent slab (2), the reflective layer (5) being adapted to reflect light reaching the reflective layer from the backside (4) of the translucent slab (2), wherein the translucent slab (2) comprises pores (6), wherein the pores (6) are dead end pores (6) extending from respective openings (7) at the front side (3) into the translucent slab (2), through the reflective layer (5), wherein a cross-sectional dimension of the openings (7) of the pores (6) is dimensioned so as to prevent larger particles or debris, if any
(Continued)

included the fluid, from entering the pores (6), while allowing the analyte (96) in the fluid (99) to enter the pores (6) via diffusion.

24 Claims, 6 Drawing Sheets

(51) Int. Cl.
B01L 3/00 (2006.01)
G01N 33/72 (2006.01)
G01N 21/03 (2006.01)
A61B 5/00 (2006.01)
G01N 15/00 (2006.01)
A61B 5/15 (2006.01)

(52) U.S. Cl.
CPC ......... *G01N 33/491* (2013.01); *G01N 33/728* (2013.01); *A61B 5/0075* (2013.01); *A61B 5/15* (2013.01); *B01L 3/502753* (2013.01); *G01N 2015/0065* (2013.01); *G01N 2021/0357* (2013.01); *G01N 2201/061* (2013.01)

(56) References Cited

U.S. PATENT DOCUMENTS

| | | | | |
|---|---|---|---|---|
| 7,959,791 | B2* | 6/2011 | Kjaer | C12Q 1/002 205/778 |
| 10,663,395 | B2* | 5/2020 | Kjaer | G01N 33/491 |
| 2004/0201835 | A1* | 10/2004 | Coates | G01N 21/552 356/73 |
| 2005/0191620 | A1 | 9/2005 | McDevitt et al. | |
| 2006/0257854 | A1 | 11/2006 | McDevitt et al. | |
| 2006/0275857 | A1* | 12/2006 | Kjaer | C12Q 1/002 435/23 |
| 2012/0086021 | A1* | 4/2012 | Wang | G01N 21/658 257/84 |
| 2012/0194813 | A1* | 8/2012 | Tzeng | G01N 21/658 356/301 |
| 2012/0238840 | A1* | 9/2012 | Hashimoto | A61B 5/1455 600/310 |
| 2013/0114076 | A1* | 5/2013 | Schleipen | A61B 5/0059 356/246 |
| 2013/0184188 | A1 | 7/2013 | Ewart et al. | |
| 2014/0118745 | A1* | 5/2014 | Neijzen | G01N 21/552 356/432 |
| 2014/0193892 | A1 | 7/2014 | Mohan et al. | |
| 2014/0211206 | A1* | 7/2014 | Wang | G01N 21/658 356/300 |
| 2014/0327909 | A1* | 11/2014 | Kall | G01N 21/4133 356/327 |
| 2015/0131092 | A1* | 5/2015 | Sakagami | G01N 21/658 356/301 |
| 2015/0168371 | A1* | 6/2015 | Babson | G01N 33/49 356/40 |
| 2015/0293016 | A1* | 10/2015 | Perkins | C25D 5/10 356/70 |
| 2017/0241899 | A1* | 8/2017 | Jones | G01N 21/314 |
| 2020/0256845 | A1* | 8/2020 | Kjaer | G01N 21/31 |

FOREIGN PATENT DOCUMENTS

| | | |
|---|---|---|
| CN | 102077072 A | 5/2011 |
| CN | 102834717 A | 12/2012 |
| CN | 102959384 A | 3/2013 |
| EP | 1 256 797 | 11/2002 |
| GB | 2 090 659 | 7/1982 |
| JP | 59-214765 | 12/1984 |
| JP | 2003-4733 | 1/2003 |
| JP | 2004-532338 | 10/2004 |
| JP | 2007-175514 | 7/2007 |
| JP | 2007-523321 | 8/2007 |
| JP | 2010-503002 | 1/2010 |
| JP | 2010-204011 | 9/2010 |
| JP | 2012-522249 | 9/2012 |
| JP | 2013-164372 | 8/2013 |
| WO | WO 2005/062986 | 7/2005 |
| WO | WO 2014/024066 | 2/2014 |
| WO | WO 2014/105070 A1 | 7/2014 |
| WO | WO 2015/010709 A2 | 1/2015 |

OTHER PUBLICATIONS

Crowley, Timothy A. et al., "Isolation of plasma from whole blood using planar microfilters for lab-on-a-chip applications," Lab on a Chip, vol. 5, No. 9, pp. 9220929 (2005).

Miney, Paul G. et al., "A New Optically Reflective Thin Layer Electrode (ORTLE) Window: Gold on a Thin Porous Alumina Film Listed to Observe the Onset of Water Reduction," Electroanalysis, vol. 16, No. 1-2, pp. 113-119 (2004).

International Search Report for International Application No. PCT/EP2016/077943, dated Jan. 30, 2017.

Written Opinion of the International Search Authority for International Application No. PCT/EP2016/077943.

* cited by examiner

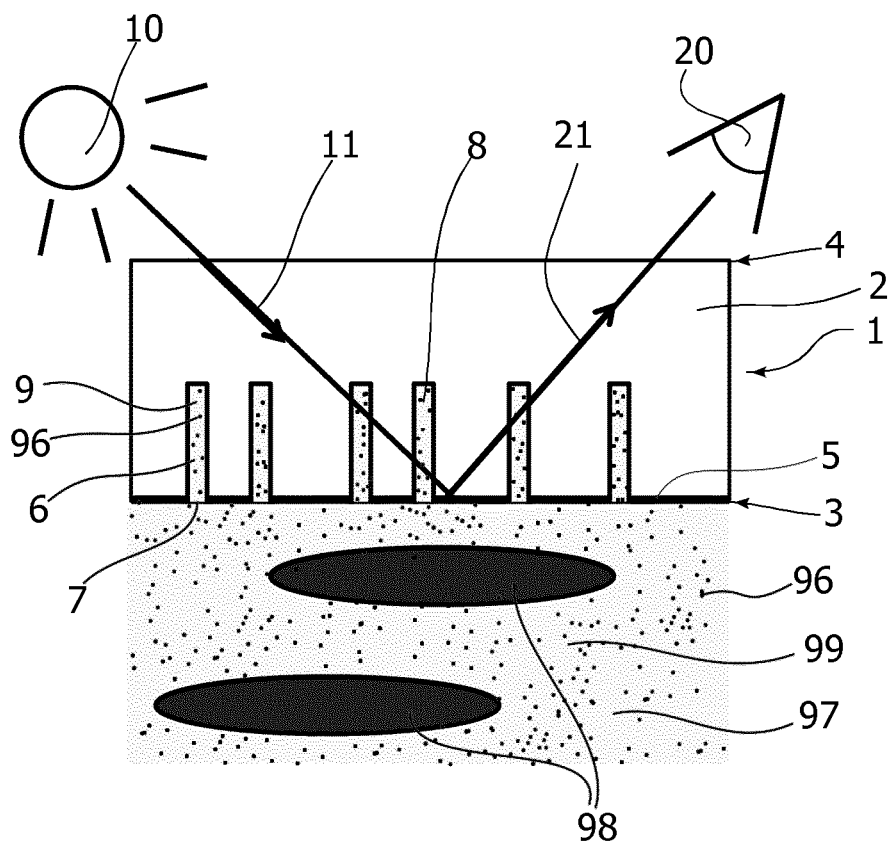
Fig. 1
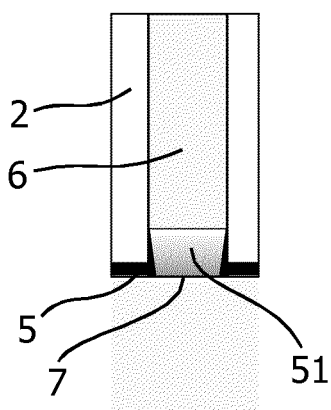 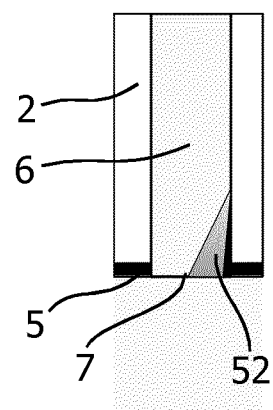 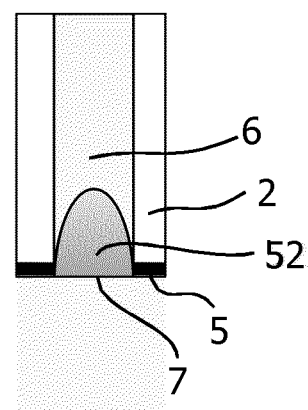
Fig. 2　　　　Fig. 3a　　Fig. 3b

POROUS MIRROR FOR OPTICAL DETECTION OF AN ANALYTE IN A FLUID

This application is a continuation of U.S. patent application Ser. No. 15/776,469, filed on May 16, 2018, which is a national stage filing under 35 U.S.C. § 371 of International Application No. PCT/EP2016/077943, filed on Nov. 17, 2016, which claims priority of Danish Patent Application No. PA 2015 00740, filed on Nov. 18, 2015. The contents of these applications are each incorporated herein by reference.

The present invention relates in one aspect to a porous mirror for use in the optical detection of an analyte in a fluid. In a further aspect, the present invention relates to a system for analyzing a fraction of a fluid comprising a porous mirror for the optical detection of an analyte in the fluid. According to a further aspect of the invention, a system for analyzing whole blood comprises optically detecting bilirubin. According to a yet further aspect of the invention, a method is provided for optically detecting an analyte in a fluid.

According to a broader aspect, the present invention relates to a porous mirror for use in the optical detection of substances in a fraction of a fluid. In a further aspect, the present invention relates to a porous mirror for the optical detection of substances in the plasma fraction of a whole blood sample. According to a further aspect of the invention, a system for analyzing a fluid comprising a porous mirror for the optical detection of substances in a fraction of the fluid. According to a yet further aspect of the invention, a method is provided for optically detecting substances in the plasma fraction of whole blood. Further, a method for analyzing a fluid comprises optically detecting substances in a fraction of the fluid.

BACKGROUND OF THE INVENTION

There are many different ways of detecting a subset of molecules in a fluid. Variations are from membranes, to chemical methods and biological processes. Many known processes utilize external forces for the filtration part, which can have detrimental effect on the filtrate. Other methods utilize a multi-step process with the initial step of filtering, followed by a detection step. This can lead to complex processes.

A one-step means for filtering and detecting a subset of molecules is relevant in a diverse field of technologies, ranging from food industry, to waste water treatment, drugs and medical devices.

Within the field of medical devices most traditional methods of filtering and detecting comprise large volumes of the fluid needing filtration. Detecting drugs in e.g. whole blood is often not possible and a larger volume whole blood is drawn from the patient due to the need of plasma for the analysis of the drug of interest. If the analysis is needed often the veins of the patient is punctured regularly and there is a risk of anemia for the patient.

Within the field of food industry, such as a dairy industry most traditional methods of filtering and detecting comprise filter paper, sieves and the like for visual inspection, spectrometry or bacterial counting of the residues. Disadvantages of this is large volumes are needed and that it is time consuming.

Within the field of environmental technologies, such as waste water analysis and treatment most traditional methods of filtering and detecting comprise filter papers, sieves and the like for spectrometry and bacterial counting of the residues. Disadvantages of this are the same as for the food industry; large volumes and time consuming.

One use of a porous mirror is in relation to detection of an analyte in a patient sample. The analyte can be any of a laboratory's test parameters for blood analysis which is detectable by light, e.g. spectrophotometry. Other approaches for measuring components present in a fraction of a fluid containing particles or other debris involve the separation of a fraction from cellular components by microfiltration techniques in e.g. a microfluidic device, prior to analysis of the fraction in a dedicated measurement in the microfluidic device. For example, a scientific article by Archibong et al. and published in Sensing and Bio-Sensing Research 3 (2015), p. 1-6, discloses a miniature measuring chamber for optically analyzing a plasma fraction that has been separated from a whole blood sample. In this type of device, a miniature microfluidic chamber is attached to the interface of an optical fiber. The bottom of the microfluidic chamber consists of a porous membrane that allows fluids and chemical compounds to flow inside the device, while at the same time filtering out undesired particles. The inside of the microfluidic chamber receiving the filtrate can be optically probed through a single optical fiber in normal-incidence reflection geometry.

However, such filtration-based approaches have several disadvantages when used for analyzing e.g. whole blood samples. Filtration devices inherently rely on a fluid flow of at least the filtrate through the pores of the filter from a sample feed to a filtrate analysis/measurement chamber. In through-flow geometries, the retentate (here the red blood cells) gradually clogs the filtration pores. In crossflow geometries, the retentate is lead along the surface of the filtering membrane, thereby reducing but not removing the problem with clogging, especially if the system is intended for repetitive use (more than 10-100 samples). Crossflow geometry also induces friction and shear interaction between the retentate and the surface of the filtering device. The disclosed device is most useful as a disposable rather than for continued and repetitive use, since a complete washout of a sample after measurement may be difficult or at least very time-consuming and unreliable, at the further risk of cross-contamination between subsequent samples. In this particular type of device, additional challenges for obtaining quantitative results from the optical probing may arise, due to pressure-induced deformation of the filtration membrane resulting in a change of the optical path for probing the filtrate.

Therefore, there is a need for an improved device and method for the detection of an analyte in a fluid with a fast and reliable response. More generally, there is a need for an improved device and method for the detection of substances in a fraction of a whole blood sample with a fast and reliable response.

Object of the present invention is to provide an improved detection overcoming at least some of the disadvantages of known sensors, systems and or methods for detecting substances in the plasma fraction of a whole blood sample, and in particular for detecting an analyte in a fluid.

The advantage of the present invention is that the filtration is performed by diffusion where no external energy is needed and the diffusion is also fast so that measurement on the liquid that have diffused into the pores of the porous mirror can be performed shortly after the fluid has been introduced into the porous mirror. The porous mirror is simple, with few parts and none that needs moving or changing position during filtration and measurement. The porous mirror is small in size and the volume needed for a measurement is very small compared to regular filtration devices. The porous mirror could be included into other applications or devices where filtration and subsequent measurement is needed on a fluid.

SUMMARY OF THE INVENTION

A first aspect of the invention relates to a porous mirror for the optical detection of an analyte in a fluid, the porous mirror comprising a translucent slab with a front side and a back side facing away from the front side, wherein the front side is adapted for being contacted with a fluid; a reflective layer at the front side of the translucent slab, the reflective layer being adapted to reflect light reaching the reflective layer from the translucent slab; wherein the translucent slab is provided with dead end pores extending from respective openings at the front side into the translucent slab, wherein a cross-sectional dimension of the openings of the pores is dimensioned so as to prevent particles or debris, e.g. red blood cells when the fluid is whole blood, from entering the pores, while allowing the analyte in the fluid to enter the pores.

The term "fluid" refers to whole blood sample, the plasma fraction of whole blood, spinal cord fluid, urine, pleura, ascites, wastewater, a pre-prepared fluid for any kind of injection, fluids with a constituent possible to detect by spectroscopy, or a gas such as air, carbon dioxide containing gas, carbon monoxide containing gas.

The term "sample" refers to the part of the fluid that is used or needed in the analysis with the porous mirror of the invention.

The term "whole blood" refers to blood composed of blood plasma, and cellular components. The plasma represents about 50%-60% of the volume, and cellular components represent about 40%-50% of the volume. The cellular components are erythrocytes (red blood cells), leucocytes (white blood cells), and thrombocytes (platelets). Preferably, the term "whole blood" refers to whole blood of a human subject, but may also refer to whole blood of an animal. Erythrocytes constitute about 90%-99% of the total number of all blood cells. They are shaped as biconcave discs of about 7 µm in diameter with a thickness of about 2 µm in an un-deformed state. The erythrocytes are highly flexible, which allows them to pass through very narrow capillaries, reducing their diameter down to about 1.5 µm. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Leucocytes make up less than about 1% of the total number of all blood cells. They have a diameter of about 6 to about 20 µm. Leucocytes participate in the body's immune system e.g. against bacterial or viral invasion. Thrombocytes are the smallest blood cells with a length of about 2 to about 4 µm and a thickness of about 0.9 to about 1.3 µm. They are cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50%-60% by volume). Plasma is devoid of cells. It contains all coagulation factors, in particular fibrinogen and comprises about 90%-95% water, by volume. Plasma components include electrolytes, lipid metabolism substances, markers, e.g. for infections or tumors, enzymes, substrates, proteins and further molecular components.

The term "wastewater" refers to water that has been used, as for washing, flushing, or in a manufacturing process, and so contains waste products and/or particles and is thus not suitable for drinking and food preparation.

The term "translucent" refers to a material's property of allowing light to pass through. The term "transparent" refers to the property of a material of allowing light to pass through the material without being scattered. The term "transparent" is thus considered a sub-set to the term "translucent".

The porous mirror comprises a translucent slab and a reflecting layer applied to a front side of the translucent slab. The translucent slab contains small, dead end pores extending from the front side, through the reflective layer into the translucent slab. The porous mirror needs a light source and a detector arranged to optically probe the content of the pores, and to generate a corresponding signal output representative of the analyte content in a fluid.

Each of the small pores has an opening through which it can communicate with a fluid space at the front side of the translucent slab. The pores thus penetrate the reflecting layer to allow for fluid communication between the pores and the fluid space. The pores extend from the respective opening at the front side into the translucent slab in a direction towards the backside. The pores are "dead end" meaning that the pores end within the translucent slab. The pores do not continue all the way through the translucent slab to the backside or to any common reservoir or recipient inside the slab. The pores are only in fluid communication with the fluid space at the front side of the translucent slab. Note that in some embodiments the dead end pores can be crisscrossing and at least some of the pores may thus be connected to each other forming an X-shape, a Y-shape, a V-shape, or similar interconnected shapes. Such a configuration is equally considered as dead end, since the pores are only filled from the front side and no significant net mass transport passing through the pores occurs under operation, even if they cross each other. By appropriately dimensioning the opening of the pores at the front side it is possible to prevent e.g. red blood cells of a whole blood sample or debris in the fluid on the front side of the porous mirror from entering the pores, while allowing relevant components in the plasma fraction of the whole blood sample or in the fluid to enter the pores, wherein relevant components are substances present in the plasma fraction of the whole blood sample and that are to be measured/detected using the sensor. In particular, bilirubin and carbon dioxide are relevant components.

Under operation, the front side of the translucent slab is contacted with a whole blood sample or a fluid. The small pores in the translucent slab communicate with the whole blood sample or fluid through the openings in the front side. The pore openings are dimensioned to selectively extract a sub-sample of the plasma phase of the whole blood sample or to extract a sub-sample of the fluid including the analyte. No red blood cells can enter the pores through the openings on the front side of the translucent slab. Nothing larger than the pore diameter can enter the pores which excludes e.g. any debris included in the fluid. As mentioned, the pores are dead end, only communicating with the front side of the translucent slab, i.e. the sub-sample is extracted for optical probing inside the pores and after the measurement discharged again through the same openings in the front side of the translucent slab. The sub-sample volume corresponds to the total internal volume of the pores. No filtration and net mass transport of any filtrate occurs through the pore containing layer—neither into any common filtrate recipient nor to any filtrate outlet. The optical detection will then be performed only on the sub-sample contained in the pores.

The reflective layer optically separates the optical probing region in the translucent slab from the fluid space containing the whole blood sample or the fluid. By optically separating the probing region from the fluid space, any contribution of the intact red blood cells of the whole blood sample or of the debris in the fluid to the probed signal can be effectively suppressed. The measurement is thus specific to the content of analyte in the fluid.

The small sub-sample with a representative content of the relevant components may be transferred to the pores in any suitable manner. The small dead end pores allow for a very efficient and fast extraction of the sub-sample for optical probing from a whole blood sample or a fluid through the openings in the front side by means of capillary forces and/or diffusion.

In a typical operation mode, the front side surface of the translucent slab is contacted by a rinsing fluid prior to contacting the front side with a whole blood sample or fluid that is to be analyzed. Thereby, the pores are 'primed' with a prefill of a liquid that is compatible with the whole blood sample or the fluid, and in particular a liquid that is compatible with the plasma phase if the fluid is whole blood, such as an aqueous solution commonly used for rinse, calibration and/or quality control purposes in blood analyzers. Typical rinse liquids used for e.g. wash-out in whole blood analyzer systems may be used as such a liquid. Rinse liquids are aqueous solutions comprising $K^+$, $Na^+$, $Cl^-$, $Ca^{2+}$, $O_2$, pH, $CO_2$, and $HCO_3^-$ in concentrations corresponding to human plasma. Non-limiting examples of suitable solutions commonly used for rinse, calibration and/or quality control purposes are given further below. When the whole blood sample or fluid is then brought in contact with the front side surface that is primed with a plasma compatible liquid/fluid compatible liquid, a representative sub-sample of components in the plasma phase of the whole blood sample or of the fluid is extracted and transferred in a very efficient and gentle manner by means of diffusion of the relevant components into the prefilled pore. In particular, any concentration gradient in the content of the analyte between the fluid and the reference liquid in the pores drives a diffusive transfer, thereby producing in the pores a sub-sample with an analyte concentration representative of the analyte concentration in the fluid.

In another operation mode, it may also be conceived to directly contact the front side of a dry sensor with a whole blood sample or a fluid. Further preferably in this operation mode, an inside surface of the pores is hydrophilic, thereby extracting the sub-sample from the whole blood sample or fluid at the front side of the translucent slab into the pores by means of capillary forces. When operating a porous mirror in this mode calibration could occur either via batch calibration as porous mirrors produced from the same batch of porous membrane material tend to have equal sensitivity (equal light absorption when measuring on identical fluids using porous mirrors produced from different pieces of porous membrane material from the same batch forming the translucent slab). Alternatively, the pores of the translucent slab can contain a calibration dye with absorption characteristics different from the analyte. The calibration dye is useful for normalizing/calibrating the optical probing signal, while being spectrally distinguishable from the substance in a plasma sample, e.g. bilirubin, to be detected/measured. Since the calibration dye will not be present in the actual fluid, the calibrant dye will diffuse out of the sensor during the measurement, meanwhile the analyte diffuses into the pores of the sensor. By optically probing the pores before and after acquiring the fluid, a quantitative measure for the substance to be detected (e.g. bilirubin) may be developed by a comparison of the calibration reference and fluid substance signals.

The content of the pores can conveniently be probed optically from the back side of the translucent slab, or more generally, from the side of the reflective layer facing towards the translucent slab, wherein the reflective layer optically separates an optical probing region comprising the pores from the fluid contacting the front side of the translucent slab. The reflective layer is adapted to reflect light reaching the reflective layer from the inside of the translucent slab, thereby preventing probing light from reaching and interacting with the fluid at the front side of the mirror. The optical probing is thus selectively performed only on the sub-sample inside the pores.

The porous mirror may be connected to a light source and a light detector configured for optically probing the translucent slab, the light source should be adapted to illuminate at least the pores, and the detector should be arranged to receive light emerging from the pores in response to an illumination by the light source, and the detector should also be adapted to generate a signal representative of the detected light.

Incident light is guided/directed to the optical probing region to ensure that the light traverses the pores and interacts with the sub-sample therein. Preferably, the probing light is sent into the probing region at an oblique incidence with respect to a surface normal on the plane of the reflective layer, to ensure that the light traverses the pores filled with the fluid to be probed, thereby ensuring a maximum of optical interaction path length.

Light emerging from the pores in response to the illumination has interacted with the sub-sample in the pores and thus carries information on the sub-sample. The emerging light and/or a signal representative of the emerging light may then be analyzed with respect to that information in order to develop a value representative of the analyte content in the whole blood sample or in the fluid. Analysis may include spectrally analyzing the emerging/detected light, and/or signal/data processing, e.g. for comparing the obtained signal with signals obtained on calibration/reference samples, for noise filtering, for applying corrections, and for removing artefacts.

In a particularly advantageous embodiment, it is the coloring of the plasma by bilirubin that is probed optically, e.g. by using spectrally resolved absorbance measurements, or by measuring the spectrally integrated absorbance over a predetermined bandwidth within a spectral range indicative of the presence of bilirubin in the liquid sub-sample, such as within a spectral range of wavelengths 380 nm-750 nm, such as within a spectral range of wavelengths 400 nm-520 nm, or at about 455 nm.

Further according to one embodiment of a porous mirror according to the invention, a cross-sectional dimension of the openings of the pores is about 1 µm or less, about 800 nm or less, preferably about 500 nm or less, or even about 400 nm or less, and/or a length of the pores in an axial direction along the pores is less than 100 µm, less than 50 µm, preferably less than 30 µm, or about 25 µm.

By using pores having an opening in the plane of the front side of the translucent slab with a maximum cross-sectional dimension of about 1 µm or less, or preferably in the submicron range, such as about 800 nm or less, such as about 500 nm or less, or even about 400 nm or less, any cellular components including erythrocytes, leucocytes, and thrombocytes (platelets), are prevented from entering the pores.

Further surprisingly, pores with an opening having a cross-sectional-dimension of about 500 nm or less have an increased sensitivity as compared to larger pores, such as pores having an opening with a cross-sectional dimension of about 800 nm or above, but having the same total pore volume/volume porosity.

Most preferably, the pores have a minimum opening with a respective minimum pore volume to allow for the efficient extraction of a sufficiently large sub-sample that can still be probed with an acceptable signal to noise ratio. Advantageously, the pores have an opening of about 30 nm or more, or 50 nm or more, or 100 nm or more, or about 200 nm or more.

Suitable pores may be produced e.g. from transparent polymer membranes with so-called track-etched pores, similar to those available from the company IT4IP (IT4IP s.a./avenue Jean-Etienne Lenoir 1/1348 Louvain-la-Neuve/Belgium) with the modification that the pores are closed at one end. Through-going pores in the membranes may be closed e.g. by laminating a backing sheet to the backside of the porous membrane, or by decelerating the ions such that the ion-bombardment tracks, and thus the pores etched following these tracks, stop within the transparent polymer membrane to form dead end pores. The membrane is typically backed by a stiff transparent element to provide adequate mechanical strength to the translucent slab.

The transparent slab should preferably be made of a material that does not absorb light and at the same time it should be possible to produce the dead end pores in the material e.g. by track etching the material. Material suitable for this is polyethylene terephthalate (PET or PETE) or an analogue of PET (polyethylene terephthalate polyester (PETP or PET-P)) or a polycarbonate (PC). The transparent slab may comprise a hydrophilic coating of e.g. polyethylene glycol (PEG) to increase the diffusion into the pores. The hydrophilic coating may be chosen according to the use of the porous mirror. In some use cases, the porous mirror will never dry out, once it is in use and it therefore only needs to be hydrophilic at startup. For other uses of the porous mirror, it needs coating that keeps it hydrophilic permanently for allowing the porous mirror to dry out and still be useable afterwards when the porous mirror is re-wetted for a further use.

Further according to one embodiment of a porous mirror according to the invention, a porosity of a given volume of the translucent slab comprising pores is between 50% and 5% by volume, between 30% and 10% by volume, or about 15% by volume.

The pores create porosity in the translucent slab (or in a given region of the translucent slab) with a corresponding front side surface area over which the openings of the pores are distributed. The porosity may be characterized in terms of the volume of the voids created in the translucent slab by the pores, i.e. the pore volume, wherein the pore volume is referred to the volume of the translucent slab penetrated by the pores. This volume is here defined as the volume between the front side area over which the pores are distributed and the identical parallel area shifted into the translucent slab by the maximum depth of penetration of the pores into the translucent slab as seen in an axial direction perpendicular to the front side of the translucent slab.

In addition thereto, the porosity may be further characterized in terms of the integrated pore volume, which is equal to the sub-sample volume that is available for optical probing. The pore volume may conveniently be expressed as an equivalent pore volume depth DELTA, which is the pore volume referred to the corresponding front side area over which the pore openings are distributed. Accordingly, the porosity of the translucent slab can be converted into an equivalent pore volume depth DELTA as follows. The pores having an opening within a given front side area A have a total pore volume V. The equivalent pore volume depth is then calculated as the total pore volume divided by the given front side area: DELTA=V/A.

Advantageously according to some embodiments, an equivalent pore volume depth DELTA is less than 20 µm, or less than 15 µm, or less than 10 µm, or in the range from 3 µm to 5 µm, wherein the equivalent pore volume depth DELTA is defined as the total volume of the pores V divided by the front side area A over which the openings of the pores are distributed. Thereby, a small sub-sample with a representative concentration of relevant components is obtained. A small sub-sample volume is desirable to promote a fast sub-sample exchange, thereby reducing response time of the porous mirror, and cycle time of measurements using the porous mirror. A small sub-sample volume is further desirable in order to avoid effects of depletion of boundary layers of a plasma fraction in a whole blood sample close to the front side of the translucent slab. Such depletion effect may otherwise occur in small, still standing samples, where e.g. red blood cells may obstruct an efficient diffusive exchange of relevant components from the volume of the whole blood sample towards the boundary layer at the front side of the translucent slab, if the equivalent pore volume depth exceeds a critical value.

Preferably, an equivalent pore volume depth DELTA is at least 1 µm, alternatively at least 2 µm, or in the range from 3 µm to 5 µm, wherein the equivalent pore volume depth is defined as above. A larger sub-sample volume is desirable to achieve a better signal-to-noise level due to a larger sub-sample volume contributing to the optically probed information on the relevant components in the plasma.

Further according to some embodiments, a useful compromise between reducing response time, reducing cycle time, and/or avoiding depletion effects in small still standing whole blood samples or fluids on the one hand, and a required or desired signal-to-noise ratio on the other hand is found for an equivalent pore volume depth DELTA in the range from 1 µm to 20 µm, preferably in the range from 2 µm to 10 µm or at about 4 µm-5 µm.

Advantageously according to one embodiment the translucent slab is supported by a translucent backing attached to the back side of the translucent slab. Thereby, an enhanced mechanical stability is achieved.

Further according to one embodiment of a porous mirror according to the invention, the transparent backing attached to the back side of the translucent slab has such a thickness that 60° prisms (i.e. no 90° corners on the outside of the translucent slab, the corners are "cut off" to obtain 60° surfaces instead) are positioned on the outside of the transparent backing for the light from the light source and to the detector is having an increased angle of incidence for the light reaching the pore zone. Having 60° prisms will also increase the chance of the light travelling inside the translucent slab because the light is reflected at the surfaces of the backing so there will be multiple reflections before the emerging light reaches the detector.

Further according to one embodiment of a porous mirror according to the invention, an inner wall surface of the pores is hydrophilic, e.g. coated with a hydrophilic coating. Thereby, an efficient capillary driven filling of dry pores with liquid is achieved. Furthermore, a hydrophilic coating prevents certain hydrophobic substances, such as hydrophobic dyes, hemoglobin, and other proteins, from depositing inside the pores that would otherwise lead to a gradual fouling of the sensor, which is difficult to wash out with an aqueous solution.

Further according to one embodiment of a porous mirror according to the invention, the light source is configured for providing an obliquely incident illuminating beam from the backside of the translucent slab, wherein an illumination angle is defined as the angle of the incident beam with respect to a surface normal of a reference plane defined by the front side of the translucent slab. Thereby, an increased optical interaction length is achieved, thus enhancing the interaction of the incident light with the content of the pores before it leaves the probing region for detection by the detector. Furthermore, penetration of probing light into the fluid through the pore openings is prevented, due to a reduced apparent cross-section of the pore openings, as well as increased scattering spreading light into the probing region rather than through the pore openings into the fluid space on the other side of the reflective layer.

The light source may in principle be any light source that transmits light in a region where the analyte in the pores absorb light in order for the system to work, but preferably the source should have a flat spectrum characteristic, i.e. the spectrum contains no peak amplitude, as a flat characteristic will give a better response. If the light source has a non-flat spectrum, i.e. the light source has a peak amplitude; a slight change in the peak may erroneously be interpreted as a change in absorption. Due to their properties with respect to size, weight, efficiency etc. light emitting diodes are often preferred. Further according to one embodiment of a sensor according to the invention, the detector is configured to collect light obliquely emerging from the backside of the translucent slab, wherein a detection angle is defined as the angle of the propagation of the emerging light towards the detector with respect to a surface normal of a reference plane defined by the front side of the translucent slab. The detector is configured to collect light emerging in response to illumination by the light source of the optical probing arrangement. Detecting light obliquely emerging from the backside of the translucent slab reduces contributions to the detected signal from light emerging from the whole blood sample and leaking back through the reflective layer into the probing region.

The detector may be a photodiode or a spectrometer that is able to detect the absorption in the entire spectrum. Alternatively, an array or diodes may be used, where each diode emits light at different wavelengths, and a photodiode is used as a detector. The diodes may be multiplexed to emit light in different intervals. The absorption is then found by comparing the lights emitted from a diode in that particular interval compared with the light detected by the photodiode.

Further according to one embodiment of a porous mirror according to the invention, a plane of incidence and a plane of detection intersect at a surface normal to enclose an azimuthal angle of at least 0 degrees, and less than 180 degrees, preferably less than 160 degrees, preferably less than 130 degrees, or preferably about 90 degrees, wherein the plane of incidence is spanned by the direction of the illuminating beam and the surface normal to the reference plane, and wherein the plane of detection is spanned by the direction of the emerging light propagation towards the detector and the surface normal to the reference plane. Thereby, contributions to the detected signal of glare from partial reflections at optical interfaces prior to passing the probing region are reduced. Such glare of light that has not interacted with the sub-sample in the probing region does not comprise relevant information and is therefore detrimental to the signal-to-noise ratio.

Optical probing light may be performed by any suitable optical probing arrangement. Such optical probing arrangement may include merely directing a beam of light to the backside of the translucent slab and directing the input of an optical detector to the illuminated region. The optical arrangement may include further optical elements improving coupling of the probing light into the translucent slab and improving coupling of the light emerging from the translucent slab into the detector input. Such optical elements may include one or more prisms and/or lens arrangements attached/glued directly to the backside of the translucent slab. Preferably, the coupling optics accommodates the "reflective" nature of the optical probing, where incoming probing light and detected emerging light are kept on the same side of the reflective layer. Further improvements may be sought in enhancing the optical interaction of the probing light with the pores, e.g. by coupling the probing light into the translucent slab at a first end, forcing the light in the probing region to essentially propagate in directions parallel to the front side of the translucent slab, along the reflective surface and traversing the pores, and collecting the emerging light from another end of the translucent slab, which may be transverse or opposite of the first end.

When light sources age, they might change characteristic, e.g. emit less light or drift may affect the peak amplitude. This may be compensated by using a feedback calibration process, where the detector measures the light received through the transparent slab in a situation where the pores in the transparent slab is expected to be clean, i.e. contain no molecules in the pores absorbing light. If the amplitude of the light received is smaller than expected, the feedback loop to the light source may control that the current or voltage to the light source is increased, to compensate for the degradation of the light source. Alternatively, if the light source has changed characteristics, the calculation of the actual absorption when measuring may adjust for this change of the emitted light compared to the original factory calibration.

Further according to one embodiment of a porous mirror according to the invention, the translucent slab is provided with further reflective elements arranged inside the pores, in a mouth portion thereof, adjacent to the opening at the front side of the translucent slab. The additional reflective elements are applied as a reflective coating on the inner wall of the pores beginning at the opening of each pore and extending into the pore. However, only a mouth portion close to the opening of the pore is covered. Providing additional reflective elements around the opening of the pores improves optical separation of the probing light from the fluid chamber, thereby preventing erroneous contributions to the probed signal from e.g. red blood cells in a whole blood sample in the fluid chamber. The reflecting coating may be any suitable metal coating as discussed below. The additional reflective elements may be produced in the same step as the reflective layer covering the front side of the translucent slab.

Further according to one embodiment of a porous mirror according to the invention, the further reflective elements are provided as a reflective coating covering only a fraction of the circumference of the mouth portion of the pores in the vicinity of the opening, wherein the fraction is about 70% or less, and preferably about 50% or less. By only partially covering the circumference of the pores a small reflector is provided in each pore with a concavely shaped reflecting surface facing towards the inside of the pores. The partial coverage may be produced, for example, by directional deposition of a metallic layer with the front side of the translucent slab inclined with respect to the direction of deposition. The openings of the pores in the plane of the front side of the translucent slab act as shadow masks. The shadow masks only allow deposition on a part of the circumferential inner wall of the pore in a mouth region thereof, i.e. close to the opening. Thereby an array of small concave mirror elements, all oriented in the same direction, may be produced.

When illuminating these small mirror elements from the concavely shaped side the resulting emerging light is directed in a preferential direction. By placing the detector in this preferential direction an improved signal-to-noise ratio is achieved as compared to other directions and as compared to embodiments without such additional small directional mirror elements.

According to some embodiments with small mirror elements, i.e. with further reflective elements having directional characteristics, an increase in intensity of the emerging light by a factor of about 3 is observed, as compared to embodiments with additional reflective elements without directional characteristics. In addition thereto, it has surprisingly been observed that a further increase by about 50% or more of the relevant signal occurs when using small mirror elements applied to the inner surface of the pores at a mouth portion thereof, e.g. when probing absorbance. This therefore results in a surprising overall improvement in S/N ratio by a factor of at least about 4 to 5.

Note that the reflecting layer at the front side of the translucent slab is still required, also when using further reflective elements, in order to ensure the optical separation of the optical probing region in the translucent slab comprising the pores from the fluid chamber containing the whole blood sample. The reflective layer on the front side of the translucent slab is also necessary, e.g. for both illuminating and detecting from the back side.

Typically, the small mirror elements are symmetric with respect to a central mirror plane. Advantageously, a plane of incidence, as determined by the incident light beam, and a detection plane, as determined by the direction of detection are also arranged symmetrically with respect to this central mirror plane. According to one simplified embodiment, the plane of incidence and the plane of detection coincide, and are parallel to the central mirror planes of the small mirror elements.

Advantageously according to one embodiment the reflective layer and/or the further reflective elements are made of metal. Such metallic coatings can be applied in a relatively cost-effective, yet well-controlled manner with adequate reflectivity.

Advantageously according to one embodiment the reflective layer is made of platinum, palladium or an alloy comprising as a principal component platinum or palladium. These materials exhibit a good reflectivity in the spectral range of the electromagnetic spectrum (deep violet to blue) that is relevant for the detection of free hemoglobin, e.g. by absorbance probing. Furthermore, these materials are biocompatible and do not e.g. introduce artificial hemolysis. Furthermore, these materials are chemically stable and in the chemical environment of a whole blood sample.

Alternatively, according to some embodiments, the reflective layer may be made of silver or aluminum. Further advantageously according to some embodiments, the surfaces of the reflective layer facing towards the fluid volume are encapsulated by an additional passivation layer, thereby enhancing the lifetime of the device, in particular when using silver or aluminum as a material for the reflective layer. A suitable passivation may be made of e.g. a thin layer of $SiO_2$ which preferably is made transparent and has to be sufficiently thin so as to not obstruct the opening of the pores. These materials may also provide a good reflectivity in the relevant spectral range and are biocompatible and chemically stable in the environment.

Advantageously according to one embodiment, the thickness of the reflective layer is between 10 nm-100 nm depending upon the used metal. Such a layer thickness allows for applying the reflective layer by an evaporation technique without clogging of the openings of the pores at the front side of the translucent slab. At the same time, the layer thickness has to be sufficient to provide adequate attenuation of light propagating to the fluid volume in order to ensure proper optical separation between the probing region and the fluid volume containing the whole blood sample or fluid. Preferably, the transmitted light is less than 5%, less than 1% or even less than 0.1% in the spectral range of detection, i.e. in the spectral range from which a signal representative of the relevant plasma component is developed, such as in the range from 380 nm to 750 nm, from 400 to 520 nm, or at about 455 nm.

Advantageously according to one embodiment the detector includes a spectrophotometer and an optical probing device is configured for the spectrophotometric analysis of the light emerging from the probing region in the translucent slab. This allows for resolving the spectral signature of one or more relevant components in the light emerging from the sub-sample in the probing region.

Further according to a particularly advantageous embodiment, the optical probing device is configured for measuring absorbance. Thereby a surprisingly significant signal is obtained with a relatively simple optical set-up. This allows for easy integration of the sensor with more complex analysis set-ups, such as a blood analyzer system.

Several optically active components can be found in blood, e.g. bilirubin, carbon dioxide ($CO_2$), Patent Blue V and methylene blue. The membrane makes it possible to detect bilirubin with a sensitivity high enough to be able to report natural adult bilirubin concentrations. The dye Patent Blue V may be used in lymphangiography and sentinel node biopsy to color lymph vessels. It may also be used in dental disclosing tablets as a stain to show dental plaque on teeth. Methylene blue is used in treatment towards high methemoglobin concentrations in patients and in as treatment of some urinary tract infections.

When analyzing the resulting spectrum from the porous mirror it became apparent that the absorption spectra from whole blood or plasma has a negative baseline. The negative baseline is caused by the porous mirror reflecting a higher proportion of the incoming light towards the detector when measuring on whole blood or plasma than compared to rinse. The effect can be seen at high wavelengths (600 to 700 nm) where hemoglobin does not absorb. The effect arises from the higher refractive index caused by the high protein content in plasma as compared to rinse. The effect is about 5 mAbs, compared to the hemoglobin having about 15 mAbs at the hemoglobin peak wavelength (416 nm). With the detector utilizing a reference determination of the light intensity from the source, it will be possible to detect protein (human serum albumin, HSA) content of whole blood samples with a detection limit of about 1-5 g/L.

The membrane construction can be used for $CO_2$ determination in the infrared region in a whole blood sample or in a fluid. $CO_2$ has several absorption peaks in the IR zone. $H_2O$ has overlapping absorption bands. The same wavelengths can be used in a porous mirror, where, the fluid path length in the membrane is about 20 µm. For a system for $CO_2$ determination it would be possible to elongate the fluid path length because $CO_2$ has such a high diffusion coefficient.

A modified porous mirror may consist of a silicone rubber slab (preferably without pores) of a thickness from 1.0 to 10 µm, laminated on a transparent support material. On top of the silicone rubber (the side facing the fluid) a porous structure is attached which allows exchange of $CO_2$ but hinders the detecting light from entering the fluid. The advantages of using the silicone rubber slab approach is that silicone rubber has open absorption windows where $CO_2$ absorbs, furthermore water is sparingly soluble in the silicone rubber. Carbon dioxide has a solubility in silicone rubber which is approximately 5 times higher than in the solubility of it in water, which also ensures a high sensitivity.

The porous mirror can be used as a reading device for color producing/consuming assays. The advantage being that it is not necessary to produce plasma before the assay.

The following types of assays may be used with the porous mirror:
  Sandwich assays, where the receptor ligand could be bound inside the membrane channels.
  Assays where one part is bound in the pores, e.g. Bromocresol Green Albumin assay, which use bromocresol green, to form a colored complex specifically with albumin. The intensity of the color, measured at 620 nm, is directly proportional to the albumin concentration in the fluid.
  Enzyme activity assays as e.g. the aspartate aminotransferase (AST) activity assay kit, where the transfer of an amino group from aspartate to aketoglutarate results in the generation of glutamate, resulting in the production of a colorimetric (450 nm) product proportional to the AST enzymatic activity present.

The porous mirror could also be used in non-medical applications such as beer brewing, wastewater analysis, food testing and in dye production. In beer brewing a precise color is desired. The porous mirror could be used to determine whether or not the beer has the desired color or not by measuring on the liquid and compare the reading with a liquid of correct color. Wastewater could be analyzed for presence or absence of a constituent. In food testing, liquids such as milk, juices and other slurries, the porous mirror could be used for analysis for presence or absence of a constituent or analyte. Other chemical reactors e.g. the dye industry could be using the porous mirror to obtain the desired color, content or other chemical properties for their liquids.

Advantageously according to some embodiments, the porous mirror or a blood analysis system comprising the porous mirror further comprises a processor configured for comparing the signal generated by the detector with a predetermined calibration reference to develop a quantitative measure of the analyte level in the fluid.

Further advantageously according to some embodiments, the calibration reference is obtained on a dye-based calibration solution, such as an aqueous solution comprising tartrazine dye. Preferably, the dye-based aqueous solution is prepared from a typical rinse liquid with the addition of the calibrant dye, such as tartrazine.

According to a further aspect of the invention a system for analyzing a fluid comprises (a) a fluid chamber with inlet and outlet ports for feeding and discharging the fluid; (b) a first detector adapted to provide a first signal representative of a level of an analyte in the fluid; and (c) one or more further detectors, each further detector being adapted to provide a respective further signal representative of an analyte of the fluid; wherein the first and further detectors are operable to obtain the first and the one or more further signals from the same fluid, wherein the first detector is configured as a porous mirror for the optical detection of an analyte according to any of the embodiments disclosed herein.

As already discussed above, by this design it is achieved that the pores can be filled from the front side with a sub-sample comprising relevant components of the plasma in representative amounts, merely by contacting the front side surface of the porous mirror with a fluid, and that the sub-sample thus extracted can conveniently be optically probed separate from the fluid. Relevant components could be substances that are present in the plasma phase of a whole blood sample and that are to be measured/detected using the sensor. A representative sub-sample of the plasma phase may be extracted from the whole blood sample and transferred into the pores by means of diffusion and/or capillary forces. As also discussed above, the pores are preferably prefilled with a liquid that is compatible with the plasma phase, such as an aqueous solution commonly used for rinse, calibration and/or quality control purposes in blood analyzers. Non-limiting examples of suitable solutions are given further below. Priming the pores with such a known liquid allows for extracting a sub-sample representative of the relevant components in the plasma into the pores by diffusion alone.

Advantageously according to an aspect of the invention, a method of optically detecting an analyte such as bilirubin in a fluid is provided as detailed in the following. The method at least achieves the same advantages as discussed above with respect to respective embodiments of a porous mirror for detecting an analyte, or of a system comprising such a porous mirror.

According to some embodiments, a method of optically detecting an analyte in a fluid comprises the steps of providing a porous mirror as disclosed above; contacting the porous mirror with a reference liquid so as to fill the pores with the reference liquid; contacting the front side of the porous mirror with a fluid; waiting for a diffusion time to allow for diffusion of the analyte in the fluid into the pores to stabilize; optically probing the fluid inside the pores; and, based on the result of the optical probing, establishing an analyte level of the fluid. Preferably, the reference liquid is an aqueous solution that is compatible with the fluid, and in particular with the fraction thereof that may enter the pores, such as a liquid for rinse, calibration and/or quality control. In some embodiments, it may be conceived to omit the step of contacting the front side of the mirror with a reference liquid prior to introducing the fluid. However, including the step allows for a purely diffusive sub-sample extraction, which is very efficient and leads to a surprisingly fast detection response and surprisingly short cycle time for the measurement. Most advantageously, an analyte is detected optically in the pores by the color change due to the presence of the analyte in representative amounts in the extracted sub-sample.

Advantageously according to some embodiments, optical probing comprises illuminating the translucent slab with probing light from the backside and performing a spectrophotometric analysis of the light emerging from the backside of the translucent slab as an optical response to the probing light.

Advantageously according to some embodiments, optical probing is measuring the absorbance.

Advantageously according to some embodiments the method further comprises the step of comparing the optical response with a predetermined calibration reference to develop a quantitative measure of the analyte level in the fluid.

Further advantageously according to some embodiments of the method, the calibration reference is obtained on a dye-based calibration solution, such as an aqueous solution comprising tartrazine dye. Preferably, the dye-based aqueous solution is prepared from a typical rinse liquid with the addition of the calibrant dye, such as tartrazine.

BRIEF DESCRIPTION OF THE DRAWINGS

Preferred embodiments of the invention will be described in more detail in connection with the appended drawings, which show in FIG. 1 schematically, a porous mirror device according to one embodiment, under operational conditions, FIG. 2 schematically, a cross-sectional detail of a pore, with an additional reflecting element, according to one embodiment;

FIGS. 3a/b schematically, two cross-sectional side views of a detail of a pore, with an additional reflecting element, according to a further embodiment;

FIG. 7 a top elevational view of the measurement cell of FIG. 6a;

DETAILED DESCRIPTION OF PREFERRED EMBODIMENTS

Figure 4:
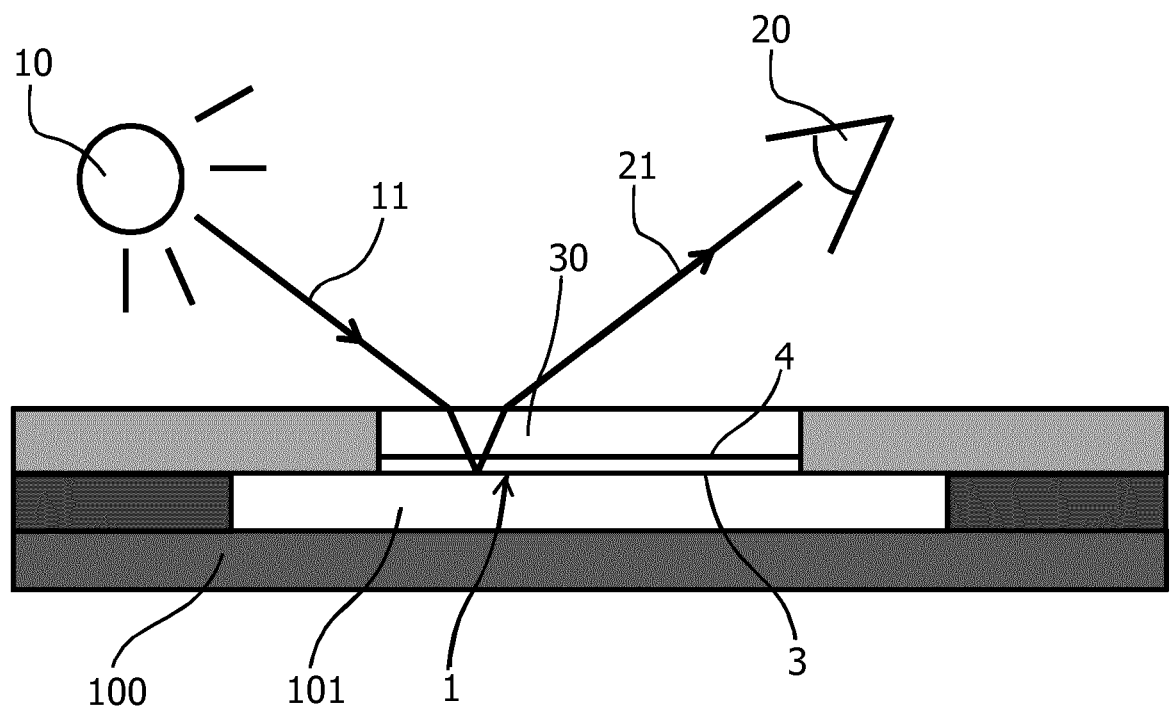
FIG. 4 schematically, a cross-sectional side view of a measurement cell.

FIG. 1 shows schematically, a cross-sectional view of a porous mirror 1 according to one embodiment. The porous mirror 1 comprises a translucent slab 2, with a front side 3 and a back side 4. The front side 3 is provided with a reflective layer 5. The translucent slab 2 further comprises dead end pores 6 extending from an opening 7 at the front side 3 through the reflective layer 5 into the bulk of the translucent slab 2, where they terminate. While shown like that in the schematic drawing of FIG. 1, the pores do not have to be perpendicular to the front side 3 or parallel to each other. Under operation, the front side 3 of the porous mirror with pore openings 7 is contacted with a fluid 99. The fluid may have a cellular fraction or particular fraction comprising red blood cells or particles 98, and a plasma fraction/fluid fraction 97 with relevant components to be detected, here the analyte 96. A cross-sectional dimension of the openings 7 of the pores 6 is dimensioned so as to prevent red blood cells or particles 98 from entering the pores 6, while allowing the analyte 96 to enter the pores 6.

The pores 6 may be pre-filled with a rinse solution 8 that is compatible with the fluid 99, and in particular with the fluid fraction 97. When the fluid 99 contacts the front side 3 of the porous mirror 1 with the pre-filled pores 6, a diffusive transfer of the analyte 96 into the pores 6 occurs, thereby establishing a sub-sample 9 inside the pores 6 with a concentration of the analyte 96 that is representative of the concentration of the analyte 96 in the fluid 99.

The rinse solution 8 used for pre-filling the pores 6 may be any aqueous solution compatible with the fluid 99. Suitable rinse solutions include those commonly used for rinse, calibration, and/or quality control purposes in blood parameter analyzers. Such solution compositions typically include organic buffers, inorganic salts, surfactant, preservatives, anti-coagulant, enzyme, colorant and sometimes metabolites. Optical detection is performed from the backside using an optical probing arrangement with a light source 10 and a detector 20. The light source 10 illuminates a probing volume in the porous portion of the translucent slab 2 from the side of the reflective layer 5 facing away from the fluid 99. The probing light 11 is an obliquely incident beam interacting with the sub-sample 9 in the pores 6. Emerging light 21 is detected by the detector 20 also arranged to view the probing region at an oblique angle. The detector 20 generates a signal representative of the emerging light, and in particular contains information on the concentration of the analyte 96, due to the interaction with the sub-sample 9 in the pores 6. Processing the generated signal allows developing a level of the analyte in the fluid. Using calibration, the level of the analyte in the fluid may be quantitative. The optical probing technique used for all measurements in the examples below uses spectrally resolved absorbance measurements in the visible range of the electromagnetic spectrum, e.g. with wavelengths in the range between about 380 nm and 750 nm, between about 400 nm and 520 nm, or at about 455 nm.

A measurement cycle is concluded by washing out the fluid with a rinse solution, such as the rinse solution 8 used for pre-filling the pores 6. Thereby, the sensor device is re-initialized and ready for receiving the next fluid.

FIG. 2 shows a detail of a porous mirror according to a further embodiment. A single pore 6 in the translucent slab 2 is shown schematically. The pore 6 comprises an additional reflective element in the form of a reflective collar 51 produced by a deposition of reflective material into a mouth portion at the opening 7 of the pore 6.

FIG. 3a and FIG. 3b show two cross-sectional views of a detail of a porous mirror according to yet a further embodiment. Again, a single pore 6 in the translucent slab 2 is shown schematically. The pore 6 comprises an additional reflective element in the form of a small mirror element 52 produced by a directional deposition of reflective material into the mouth portion at the opening 7 of the pore 6, wherein the mirror only covers a fraction of the circumference of the opening/mouth portion as indicated in the two views of FIGS. 3a and 3b. The small mirror element 52 is concave as seen from the inside of the pore. By producing the small mirror elements with directional evaporation of a suitable reflective material, preferably metal, onto an inclined porous translucent slab 2, all mirror elements 52 are formed at the same time and pointing in the same direction. Thereby, a preferential direction of the emerging light 21 is achieved when probing light 11 is incident from the concave side of the small mirror elements 52. Consequently, the signal-to-noise ratio of a signal generated from light emerging in the preferential direction is improved considerably.

All examples given below have been measured using a sensor configuration with additional small mirror elements as obtained by a directional sputter evaporation of Pd onto the front side of a translucent polymer slab 2 with a direction of evaporation at an angle of inclination of 25 degrees with respect to the surface normal on the front side 3, until a reflective layer 5 with a thickness of 30 nm on the front side 3 of the translucent slab 2 is obtained. The translucent slab 2 is made of a translucent, preferably transparent, polymer material and has track-etched dead end pores 6 with an essentially circular cross-section. The pores have an opening 7 with a diameter of 400 nm and a depth of 25 μm distributed with a porosity of 15% by volume. Together, the pores distributed over a given front side surface area A have a total volume V and have an equivalent pore volume depth DELTA=V/A. For the above specified fluid used for measurements in the examples given below, the equivalent pore volume depth DELTA is about 4 μm.

Figure 5:
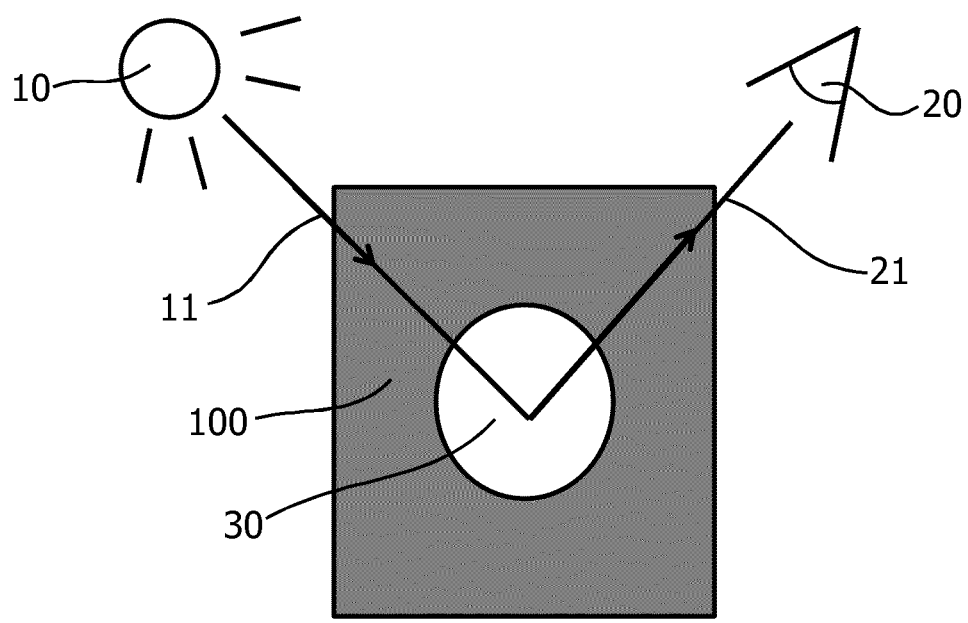
FIG. 5 a top elevational view of the measurement cell of FIG. 4.

FIG. 4 and FIG. 5 show schematically a measurement cell 100 comprising a porous mirror 1 with its front side 3 facing into a fluid volume 101 inside the measurement cell 100. The fluid volume communicates with fluid input and output ports (not shown) for feeding and discharging fluids and for performing priming, rinsing, and wash-out steps. The back side of the porous mirror is mechanically stabilized by a transparent backing slide 30, which also acts as a window for optical access to the probing region from the back side 4 of the porous mirror 1. Optical probing is performed using an arrangement with a light source 10 and a detector 20 as described above with reference to FIG. 1, wherein the probing beam and the direction of detection are inclined with respective angles to a surface normal on the plane of the front side 3 of the porous mirror 1. Furthermore, as best seen in FIG. 5, the planes of incident probing light 11 and of detection 21 preferably intersect each other with an angle of less than 180 degrees to avoid glare effects, and preferably at a pointed angle of about 90 degrees or below. In the measurements of the examples given below, the planes of incident probing light 11 and of emerging light 21 are arranged symmetrically with respect to a direction parallel to the symmetry planes of the small mirror elements 52.

Figure 6A:
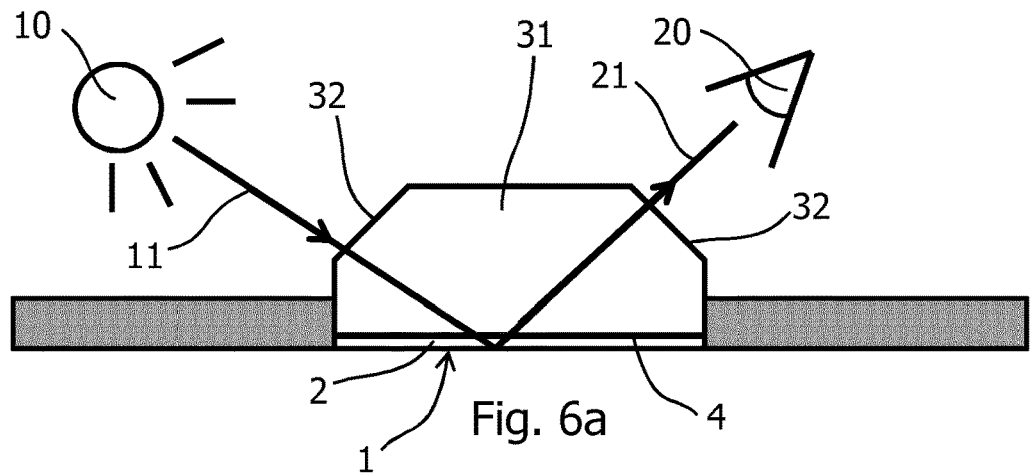
FIGS. 6a/b schematically, two cross-sectional side views of a measurement cell with prism-like outside of the transparent backing, according to a further embodiment.
Figure 6B:
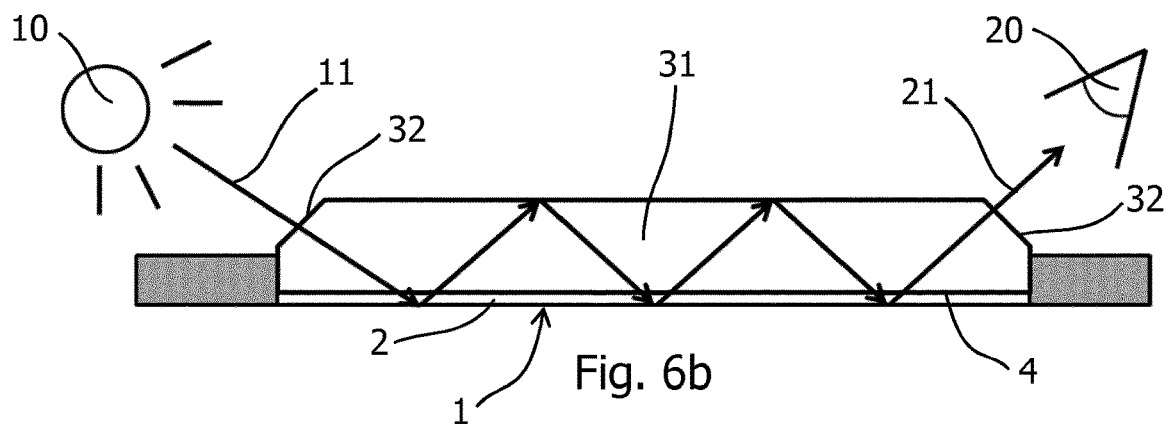
Figure 7:
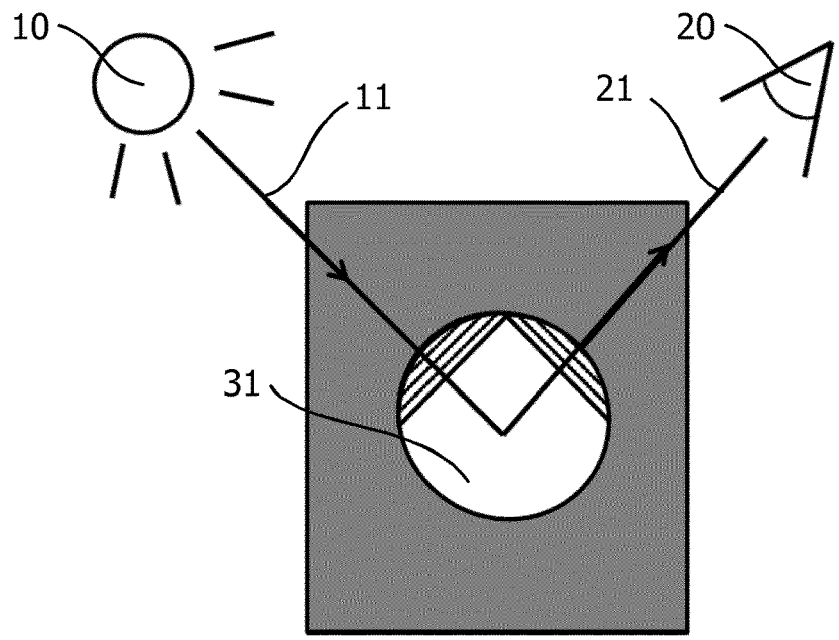

FIG. 6a, 6b and FIG. 7 show schematically a transparent backing slide 31 in direct contact with the back side 4 of the translucent slab 2 of the porous mirror 1. When incident probing light 11 enters the back side 4 of the translucent slab 2 with the surface at 60° prism 32, the shift in refractive index between air and polymer does not affect the incident probing light 11 and the light enter the pores 6 (not seen) of the translucent slab 2 without change of the angle of the light and the emerging light 21 reaches the detector 20. FIG. 6b shows that the incident probing light 11 may be reflected several times in the transparent backing slide 31 before the emerging light 21 reaches the detector 20. Furthermore, as best seen in FIG. 7, the planes of incident probing light 11 and the emerging light 21 preferably intersect each other with an angle of less than 180 degrees to avoid glare effects, and preferably at a pointed angle of about 90 degrees or below and the prisms 32 does not affect the incident probing light 11, nor the emerging light 21.

EXAMPLES

Referring to FIGS. 8-11 in the following, data from test run measurements are given as examples illustrating different aspects of the performance of a porous mirror according to an embodiment of the invention.

The porous mirror used for the experiments of these examples where produced from a transparent PETP-membrane, with a total thickness 49 μm that is provided with single-sided track-etched, linear pores. The pores have a pore depth of 25 μm and a pore diameter of 0.4 μm with a hydrophilic PVP treatment. The areal pore density is 1.2E8/cm². The pores are thus dead end with an opening at one side of the PETP-membrane, ending essentially half way into the PETP-membrane acting as the translucent slab. The porous side of the membrane (translucent slab) is sputter coated with Palladium at an angle of 25 degrees and with an approximate layer thickness of 30 nm. This gives a metal coating on the porous front-side of the membrane (translucent slab) and a small coating on one side of the inside of the pores thus forming small concave mirrors in a mouth portion of the pores adjacent to their opening towards the front side. The sputtered porous PETP-membrane is laminated to a custom build cuvette using a double sided adhesive tape so that the concave side of the small mirrors in the pores is pointing halfway between light guides from the light source and from a spectrometer input. A drop of approximately 10 μL of silicon rubber is pipetted onto the membrane and a cover glass is then fixed to the backside of the membrane as a mechanical backing of the sensor membrane (translucent slab). The porous mirror is mounted in a test bench for automatic handling of liquids, time intervals and data sampling. Data acquisition last approximately 3 s and is delayed until 14 s after fluid acquisition.

The test bench is equipped with two light emitting diodes (a purple and a 'white' LED) as light source, and with a mini-spectrometer as a detector. The standard slit in the mini-spectrometer has been replaced with a 125 μm slit in order to increase light and sensitivity. As the measurement is a reflection measurement, the light source and detector are both placed on the back side (none porous side) of the porous membrane. The porous metal coated side of the membrane is positioned on the inside of the measuring chamber and the mirror and the pores are thus directly exposed to the fluids in the chamber. Light from the two light diodes are led through a common fiber light guide, which has a lens at the end for collimating the light to a small spot of the porous mirror membrane (approximately 2 mm by 2 mm). Referring to a Cartesian coordinate °, the plane of the membrane (front side of the translucent slab) may be defined as the ZX-plane of the coordinate system. The light enters the membrane outer surface (back side of the translucent slab) at a 45° angle with respect to the Y-axis, i.e. the surface normal to the ZX-plane (and in the YZ-plane of the coordinate system). The detector is positioned with a polar angle of 60° with respect to the Y-axis, and turned with respect to the YZ-plane by an azimuthal angle of 90° with respect to the plane of incidence of the light source (e.g. in the YX-plane). The relatively high angles of light incidence and detection direction with respect to the Y-axis results in improved detection sensitivity for hemoglobin, since the collected light has traveled through a greater length of the sub-sample in the pores.

Fluids are prepared by spiking a whole blood sample with bilirubin. The interference solutions based on plasma are prepared by spiking the plasma with interferents to the specified values. Plasma is produced by centrifugation in 15 min. at 1500 G. As reference, the absorbance spectra of centrifugation derived plasma from all whole blood samples tested are also measured on a Perkin Elmer Lambda 19 UV-Vis spectrometer.

Figure 8:
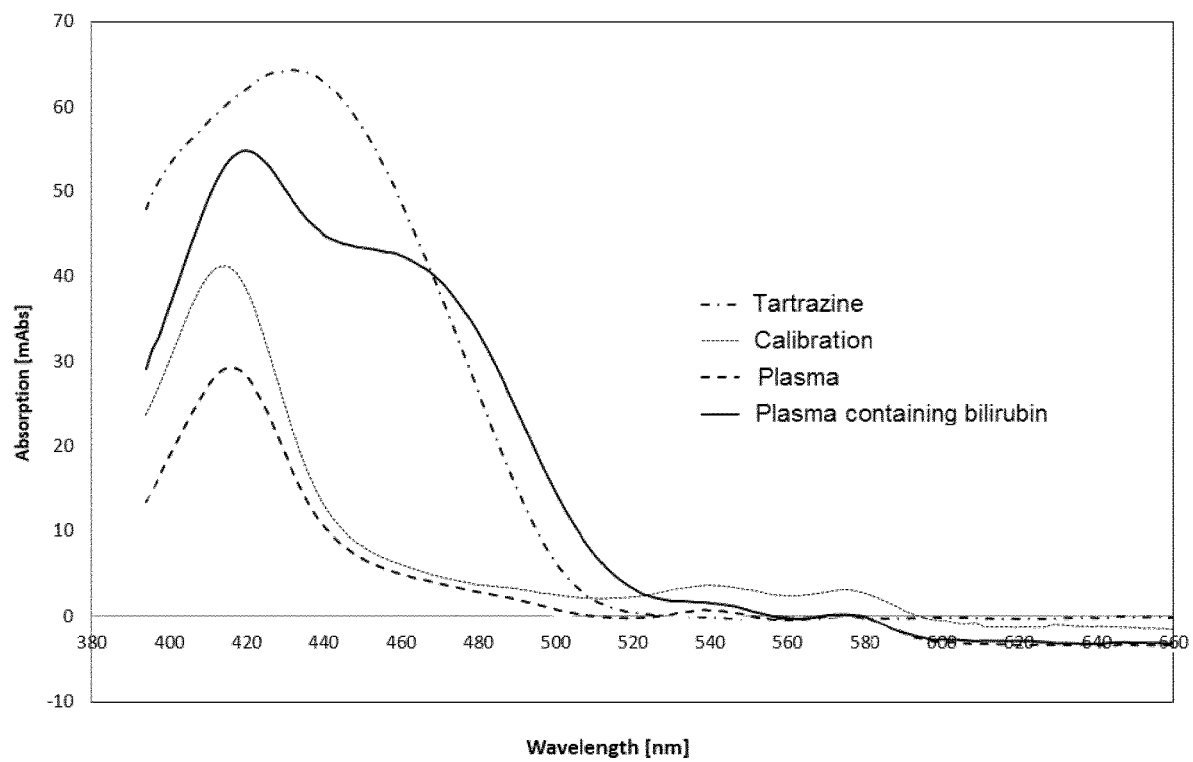
FIG. 8 a graph showing examples of response of bilirubin in plasma.

Spectral FIG. 8 shows spectrally resolved absorbance data for two fluids, one with plasma containing bilirubin and on with only plasma. At a wavelength of around 455 nm a pronounced peak is observed wherein the absorbance maximum for the different fluids evidently scales linearly according to their content in bilirubin.

Figure 9:
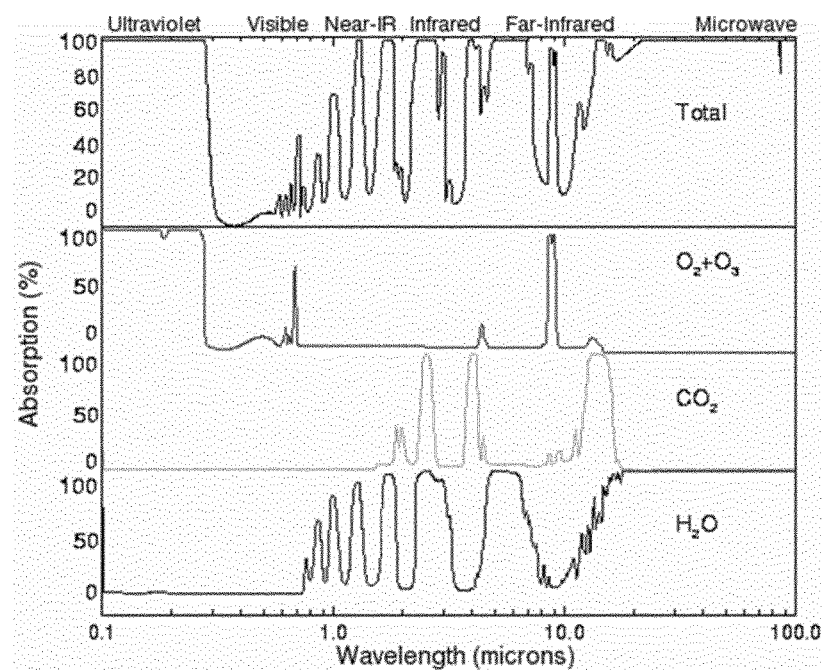
FIG. 9 a graph showing IR spectra of $CO_2$ and $H_2O$ (retrieved from http://www.randombio.com/co2.html on Nov. 8, 2016)

Spectral FIG. 9 shows spectrally resolved infra-red data of carbon dioxide ($CO_2$) and water ($H_2O$). The non-overlaying peaks from $CO_2$ compared to water indicates that the $CO_2$ content can be determined using a porous mirror of the invention in a $CO_2$ containing fluid, even if water is present in the fluid.

Figure 10:
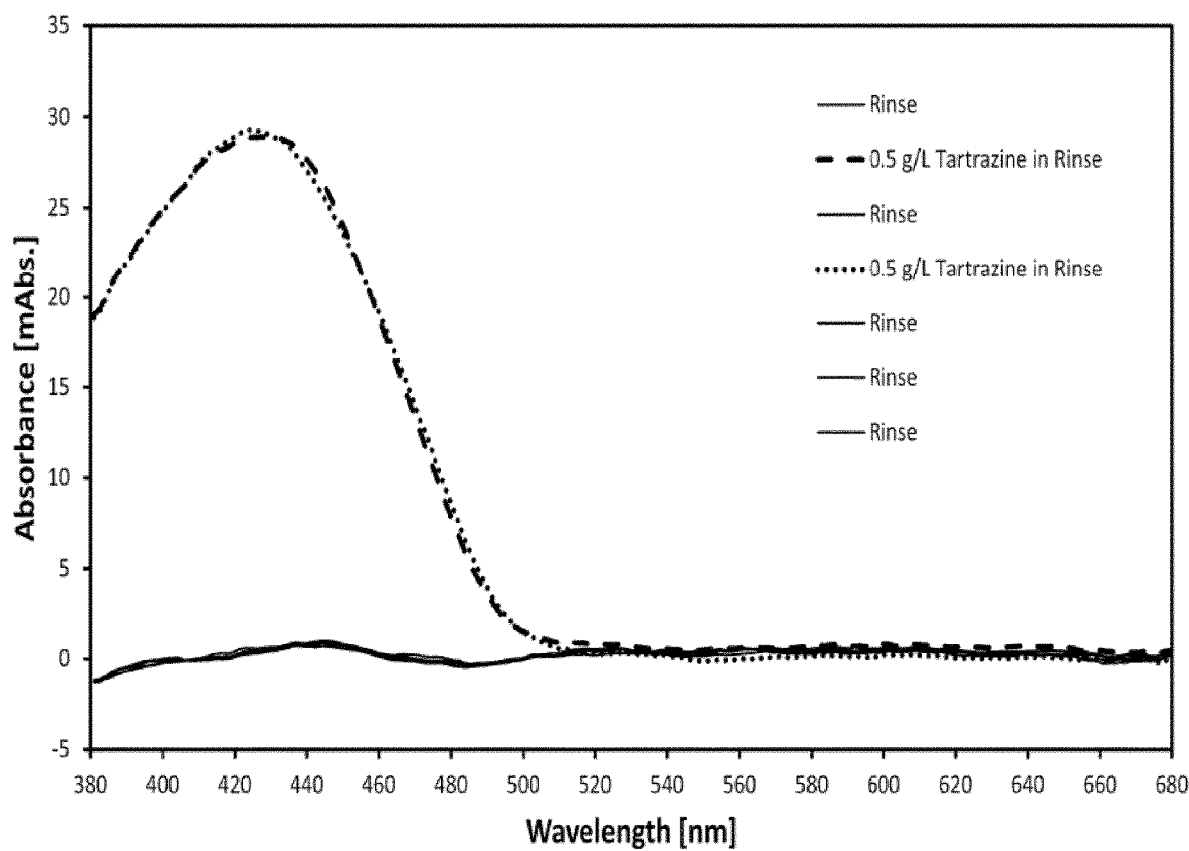
FIG. 10 a graph showing an example of using a dye (Tartrazine) as a calibration and quality control reference for spectrophotometric measurements.

Spectral FIG. 10 shows an example with a series of spectrally resolved absorbance data obtained on a dye-based calibration solution and, for comparison, on a rinse solution. The spectra where obtained in successive cycles immediately after each other. The dye-based calibration solution is a rinse solution with an addition of 0.5 g tartrazine per 1 L rinse. The sequence of measured solutions is as follows: First a rinse solution, then a dye-based calibration solution, then again a rinse solution, again the same dye-based solution and a sequence of three consecutive measurements all performed on rinse solution. All spectra are plotted on the same scale and on top of each other. The experiment shows again a very good stability and reproducibility of the obtained results. Yet more important, the data shows a surprisingly clear separation of the two dye-based solution spectra coinciding on top of each other, and all five rinse solution spectra also coinciding on top of each other. Note that the optical data are all probed in the probing volume of the porous mirror. This indicates a very efficient and complete diffusive exchange for extraction and wash-out of the sub-sample in the pores also when using a dye-based spectrophotometric calibration solution, such as the above-mentioned tartrazine dyed rinse solution.

Figure 11:
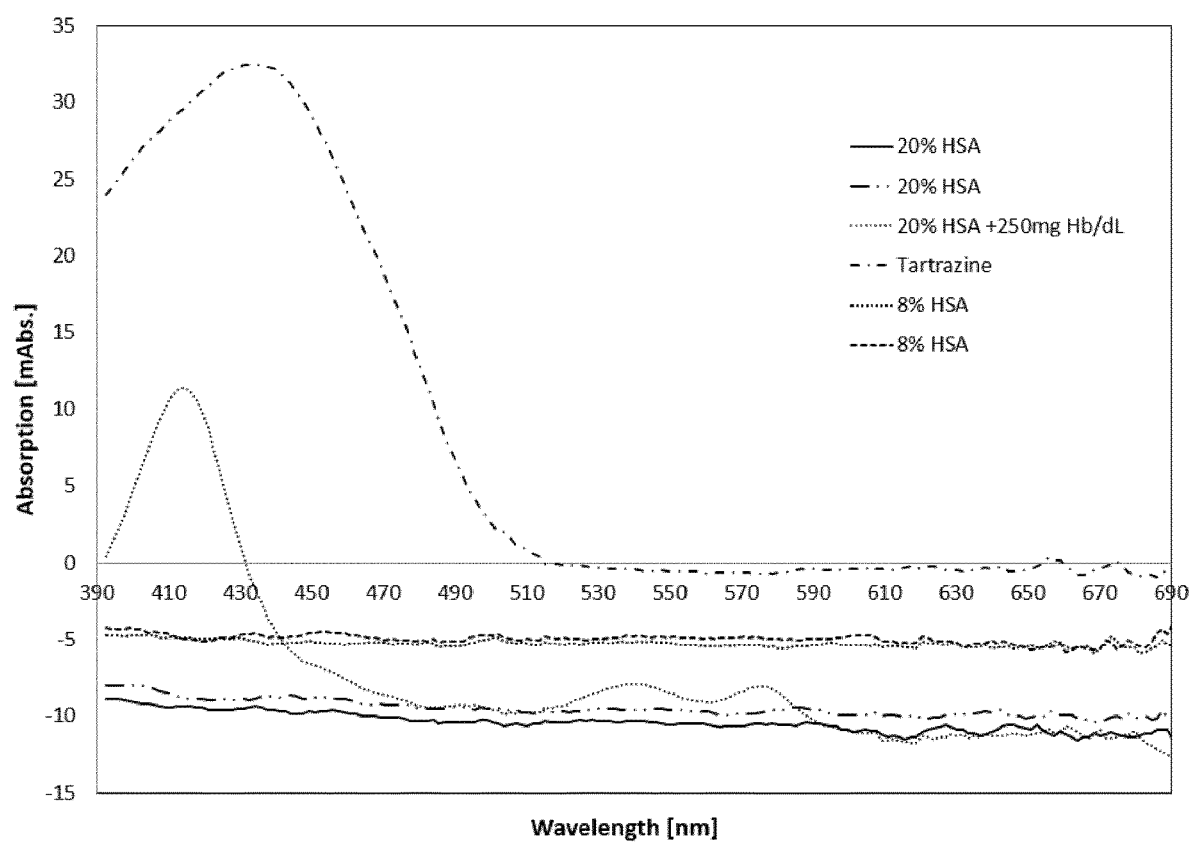
FIG. 11 a graph showing examples of response to different concentrations of protein (HSA) in human whole blood.

Spectral FIG. 11 shows spectrally resolved absorbance data of the negative baseline caused by the higher refractive index by the high protein content in plasma as compared to rinse. The porous mirror reflects a higher proportion of the incoming light towards the detector when measuring on whole blood or plasma than compared to rinse. The effect is seen at high wavelengths (600 to 700 nm) where hemoglobin in the whole blood does not absorb. The effect is about 5 mAbs, compared to the hemoglobin having about 10-15 mAbs at the hemoglobin peak wavelength (416 nm). It will be possible to detect the content of protein (HSA) of whole blood samples with a detection limit of about 1-5 g/L. Two different HSA concentrations (20% and 8%) are measured, the higher concentration is also measured with free (i.e. hemoglobin outside of red blood cells) in the fluid. The presence of hemoglobin in the fluid only affects the part of the spectra below 600 nm. Above 600 nm the HSA content is the main influence on the spectra, the more negative baseline the higher protein content in the whole blood sample.

While the device and method of the invention has been discussed specifically with reference to the detection of bilirubin, according to a broader aspect, the devices and methods discussed herein are equally applicable to the detection of other optically active substances in the plasma fraction of a whole blood sample or in a fluid, wherein "the term optically active" refers to substances, that can be detected directly by a spectroscopic optical probing technique. Such substances may include, but are not limited to metabolic substances, pharmaceutical substances, drugs, or vitamins.

The invention claimed is:

1. A device for detecting an analyte in a fluid comprising a porous mirror comprising:

a translucent article comprising (a) at least one membrane comprising pores and (b) a transparent element with a front side, and a backside facing away from the front side, wherein the front side is in contact with a fluid chamber;

a reflective layer at the front side of the translucent article, which reflects light reaching the reflective layer from the backside of the translucent article;

wherein the pores are dead end pores extending from respective openings at the front side into the at least one membrane, through the reflective layer;

wherein the pores are only in fluid communication with the fluid at the front side of the at least one membrane;

a light source, to illuminate at least the pores in the translucent article; and a light detector, wherein the detector is arranged to receive light emerging from the pores in response to an illumination by the light source, and wherein the detector generates a signal representative of the detected light.

2. The device of claim 1, wherein the fluid chamber comprises an inlet and outlet port for feeding and discharging the fluid.

3. The device of claim 1, further comprising one or more further detectors.

4. The device of claim 1, wherein a cross-sectional dimension of the openings of the pores is about 1 μm or less and/or wherein a length of the pores in an axial direction along the pores is less than 100 μm.

5. The device of claim 1, wherein a porosity of a given volume of the translucent article is between 50% and 5% by volume.

6. The device of claim 1, wherein an equivalent pore volume depth (DELTA) is less than 20 μm, wherein the equivalent pore volume depth (DELTA) is defined as the total volume of the pores (V) divided by the front side area (A) over which the openings of the pores are distributed.

7. The device of claim 1, wherein an inner wall surface of the pores is coated with a hydrophilic coating.

8. The device of claim 1, wherein the translucent article is provided with further reflective elements arranged inside the pores, in a mouth portion thereof, adjacent to the opening at the front side of the translucent article.

9. The device of claim 8, wherein the further reflective elements are provided as a reflective coating covering only a fraction of the circumference of the mouth portion of the pores in the vicinity of the opening, wherein the fraction is about 70% or less.

10. The device of claim 1, wherein a transparent backing side of the translucent article is provided with a 60° angled surface to minimize the effect of the shift in refractive index between outside air and the transparent backing slide.

11. The device of claim 1, wherein the pores are track-etched in the translucent article and reflective layer.

12. The device of claim 1, wherein the pores are rinsed by diffusion.

13. The device of claim 1, wherein at least one of the at least one membranes comprising pores is made of a transparent polymer.

14. The device of claim 1, wherein a cross-sectional dimension of the openings of the pores is about 500 nm or less and/or wherein a length of the pores in an axial direction along the pores is less than 50 μm.

15. The device of claim 1, wherein a porosity of a given volume of the translucent article is between 30% and 10% by volume.

16. The device of claim 1, wherein an equivalent pore volume depth (DELTA) is less than 10 μm, wherein the equivalent pore volume depth (DELTA) is defined as the total volume of the pores (V) divided by the front side area (A) over which the openings of the pores are distributed.

17. The device of claim 8, wherein the further reflective elements are provided as a reflective coating covering only a fraction of the circumference of the mouth portion of the pores in the vicinity of the opening, wherein the fraction is about 50% or less.

18. The device of claim 1, wherein the pores are track-etched pores.

19. The device of claim 18, wherein at least one of the at least one membranes comprising pores translucent slab is made of a transparent polymer.

20. The device of claim 1, wherein the fluid is a whole blood sample, the plasma fraction of whole blood, spinal cord fluid, urine, pleura, ascites, wastewater, a pre-prepared fluid for any kind of injection, a fluid with a constituent detectable by spectroscopy, or a gas.

21. The device of claim 1, wherein the reflective layer is made of metal.

22. A method for optically detecting an analyte in a fluid comprising providing the device according to claim 1, contacting the porous mirror with a reference liquid so as to fill the pores with the reference liquid, contacting the front side of the porous mirror with the fluid, waiting for a diffusion time to allow for diffusion of the analyte in the fluid into the pores to stabilize, optically probing the fluid inside the pores from the side of the reflective layer, and based on the result of the optical probing, establishing an analyte level of the fluid.

23. The method according to claim 22, wherein the analyte is bilirubin, carbon dioxide, Patent Blue V, or methylene blue and the fluid is whole blood.

24. The method according to claim 22, wherein the fluid is a whole blood sample, the plasma fraction of whole blood, spinal cord fluid, urine, pleura, ascites, wastewater, a pre-prepared fluid for any kind of injection, a fluid with a constituent detectable by spectroscopy, or a gas.

* * * * *

UNITED STATES PATENT AND TRADEMARK OFFICE
CERTIFICATE OF CORRECTION

PATENT NO. : 11,079,319 B2  
APPLICATION NO. : 16/854136  
DATED : August 3, 2021  
INVENTOR(S) : Thomas Kjaer Page 1 of 1

It is certified that error appears in the above-identified patent and that said Letters Patent is hereby corrected as shown below:

In the Claims

Claim 1, Column 20, Line 11, "reflective layer;" should read --reflective layer,--.

Claim 19, Column 21, Line 12, after "membranes comprising pores," "translucent slab" should be deleted.

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*